(12) United States Patent
Patil

(10) Patent No.: US 10,405,902 B2
(45) Date of Patent: Sep. 10, 2019

(54) STERNAL CLOSURE AND RIBS APPROXIMATOR DEVICES

(71) Applicant: Ajay K Patil, Rajkot (IN)

(72) Inventor: Ajay K Patil, Rajkot (IN)

( * ) Notice: Subject to any disclaimer, the term of this patent is extended or adjusted under 35 U.S.C. 154(b) by 425 days.

(21) Appl. No.: 14/396,753

(22) PCT Filed: Apr. 22, 2013

(86) PCT No.: PCT/IB2013/053159
§ 371 (c)(1),
(2) Date: Oct. 24, 2014

(87) PCT Pub. No.: WO2013/160813
PCT Pub. Date: Oct. 31, 2013

(65) Prior Publication Data
US 2015/0127004 A1    May 7, 2015

(30) Foreign Application Priority Data

Apr. 25, 2012   (IN) .......................... 1317/MUM/2012

(51) Int. Cl.
*A61B 17/82*          (2006.01)
(52) U.S. Cl.
CPC .................................. *A61B 17/823* (2013.01)
(58) Field of Classification Search
CPC ........................... A61B 17/8076; A61B 17/823
USPC .................................................... 606/74
See application file for complete search history.

(56) References Cited

U.S. PATENT DOCUMENTS 6,051,007 A  *  4/2000  Hogendijk ............. A61B 17/08
                                                    606/151
2009/0248091 A1 * 10/2009  Teague .................. A61B 17/823
                                                    606/324

OTHER PUBLICATIONS

PCT/IB2013/053159—International Search Report.

* cited by examiner

*Primary Examiner* — Si Ming Ku
(74) *Attorney, Agent, or Firm* — D'Ambrosio & Menon, PLLC; Usha Menon

(57) ABSTRACT

The present invention provides a sternal closure and ribs approximator device, the device comprising:
  a substantially C-shaped shaft/bracket, said bracket comprising: a linear shaft and a pair of curvilinear arms at either ends of the shaft, respectively; and
  a pair of claw shaped clamping elements, each claw shaped clamping element coupling with an arm of the C-shaped shaft/bracket, near its end portion, said claw shaped clamping element being positioned such that the concavity of the claw faces the inner area determined by the arms of the C-shaped clamping shaft/bracket, the coupling being provided by means of a fastening mechanism such that angular displacement of the claw shaped clamping element about the pivoted fastening mechanism is provisioned, said claw shaped clamping elements adapted to be angularly displaced towards each other or away from each other.

9 Claims, 9 Drawing Sheets

STERNAL CLOSURE AND RIBS APPROXIMATOR DEVICES

FIELD OF THE INVENTION

This invention relates to the field of mechanical engineering and devices having further use in biomedical engineering.

Particularly, this invention relates to the field of biomedical equipment.

Specifically, this invention relates to the field of surgical devices used for approximation and closure of sternum following median sternotomy for various procedures on the heart, lungs and mediasternum.

More specifically, this invention relates to a sternal closure and ribs approximator device.

BACKGROUND OF THE INVENTION

The sternum or breastbone, in vertebrate anatomy, is a flat bone. It is shaped like a capital "T" located anteriorly to the heart in the centre of the thorax (chest). It connects the rib bones via cartilage, forming the anterior section of the rib cage with them, and thus helps to protect the lungs, heart, and major blood vessels from physical trauma. Its upper end supports the clavicles, and its margins articulate with the cartilages of the first seven pairs of ribs A good number of surgical procedures on the thorax require median sternotomy. Median sternotomy provides a surgical approach to the heart and major arteries, lungs, mediastinum, and thoracic spine. The breast bone comprises a manibrium, superiorly, and a sternum, inferiorly.

Median sternotomy is a type of surgical procedure in which the sternum is cut longitudinally for entry into the thorax for exposure of heart and lungs during surgery. During surgery, the two halves of the bones are separated using retractors.

Following surgery, the sternum is approximated and held close together using various methods. Methods for re-approximation of sternum include using thin stainless steel wires, or stainless steel bands, or various sternal closure devices. Conventionally, thin stainless steel wires of about 1-1.5 mm diameter are used for closure of the sternum. Typically, a surgeon holds a needle using a strong needle holder and passes a wire around the left sternal half; either piercing the bone or going parasternal outside in. Then the wire is passed around the right sternal half inside out. The needle is cut and both the free ends of cut wires are held using clamps. After passing the required number of wires, haemostasis is checked. Then the wires are crossed individually and sternum is held closed together. The two ends of each wire are pulled across and twisted around each other so as to tighten the sternum. This procedure is repeated for all the wires. Excess wires are cut and the small twisted ends of wires are buried in the parasternal tissue to avoid cutting out of the sharp ends through skin. These wires remain permanently lodged and do not require removal unless any problem arises or unless there is a second surgical procedure.

Typically, tough stainless steel wires are widely used; but they have many disadvantages. Placement of wires often leads to bleeding from intercostals vessels during the passage of needle through parasternal tissue. Blood vessels can be punctured, leading to severe bleeding. Control of bleeding is time consuming and requires use of sutures, surgical clips, and electro cautery. This leads to increase in operating room time, exhaustion of surgical team, increase of cost of sutures and clips. Use of cautery often leads to weakening of wires and potentially decreases blood supply to the sternum leading to increased risk of sternal healing problems.

After haemostasis, during tightening of wires, some blood vessels may get injured leading to post-operative increasing drainage. This requires re-exploration and haemostasis. This again increases the cost of additional surgery, increases the risk of infection to patients. Also, additional blood and blood products are required for haemostasis and haemodynamical stability. It also results in increase of cost of antibiotics and blood and blood products, operating room time and increases strain on surgeons.

The sternum, following the surgery, has forces acting on it during breathing, coughing, and valsalva manoeuvre. This causes the sternum to retract away from each other causing stress on the stainless steel wire loops. The wires, being thin, can cut through bone leading to loosening of the sternal closure. This leads to sternal instability and risks of infection. This further leads to complete transaction of sternal bone and instability with infection called sternal dehiscence. This requires further surgical procedures, medications and antibiotics, prolonged hospital stay, and adds to the risk of mortality.

Such complications are occasionally seen in old patients or female patients with severe osteoporosis. The incidence of sternal dehiscence is also high among patients with Type II Diabetes mellitus.

Also, since the sternal wires occasionally break during tightening or during postoperative period leading to sternal instability, the broken loop often causes discomfort to the patients and protrudes out through the skin requiring second surgical procedure.

Wires and needles are sharp and can cause injury to the surgeon or the surgical team. Each cut end of wires is held in clamps and then there are several clamps in the surgical field. The cut ends often cut through the gloves and cause injuries to the surgeon/team. This accidental injury exposes the entire surgical team to blood borne diseases including AIDS, Hepatitis or the like infections or diseases or risks.

Further, the usage of stainless steel wires is often time consuming and adds on stress to the surgeon and the surgeon's team.

Other methods used for closure of sternum are sternal bands and sternal closure devices. Sternal bands are flat bands and avoid cut-through of sternums as seen in thin wires. However, bands are time consuming and difficult to apply and also the associated locking mechanism is often complex. Also during re-entry for emergency re-explorations, the bands are difficult to remove and can cause injury to underlying important organs including the heart.

Certain additional prior art clamping devices are also available for closure of sternum. Most of these devices have complex methods of applications and are also time consuming. They, however, overcome deficiencies of wire based sternal closures.

OBJECTS OF THE INVENTION

An object of the invention is to provide a relatively simple sternal closure device.

Another object of the invention is to overcome the deficiencies of wire based sternal closures.

Yet another object of the invention is to provide a single unit sternal closure device.

Still another object of the invention is to provide a sternal closure device wherein clamping/inserting components are manoeuvrable.

An additional object of the invention is to provide a sternal closure device wherein the closure of sternum is rapid and strong, thereby giving complete stability to the sternum.

Yet an additional object of the invention is to provide a sternal closure device which can be easily removed during emergency re-explorations.

SUMMARY OF THE INVENTION

According to this invention, there is provided a sternal closure and ribs approximator device, said device comprising:
- a substantially C-shaped shaft/bracket, said bracket comprising: a linear shaft and a pair of curvilinear arms at either ends of the shaft, respectively; and
- a pair of claw shaped clamping elements, each claw shaped clamping element coupling with an arm of the C-shaped shaft/bracket, near its end portion, said claw shaped clamping element being positioned such that the concavity of the claw faces the inner area determined by the arms of the C-shaped clamping shaft/bracket, the coupling being provided by means of a fastening mechanism such that angular displacement of the claw shaped clamping element about the pivoted fastening mechanism is provisioned, said claw shaped clamping elements adapted to be angularly displaced towards each other or away from each other, with the inner operative surface of each of the claw shaped clamping elements comprising a ridged surface for grasping.

BRIEF DESCRIPTION OF THE ACCOMPANYING DRAWINGS

The invention will now be described in relation to the accompanying drawings, in which.

DETAILED DESCRIPTION OF THE INVENTION

Figure 1:
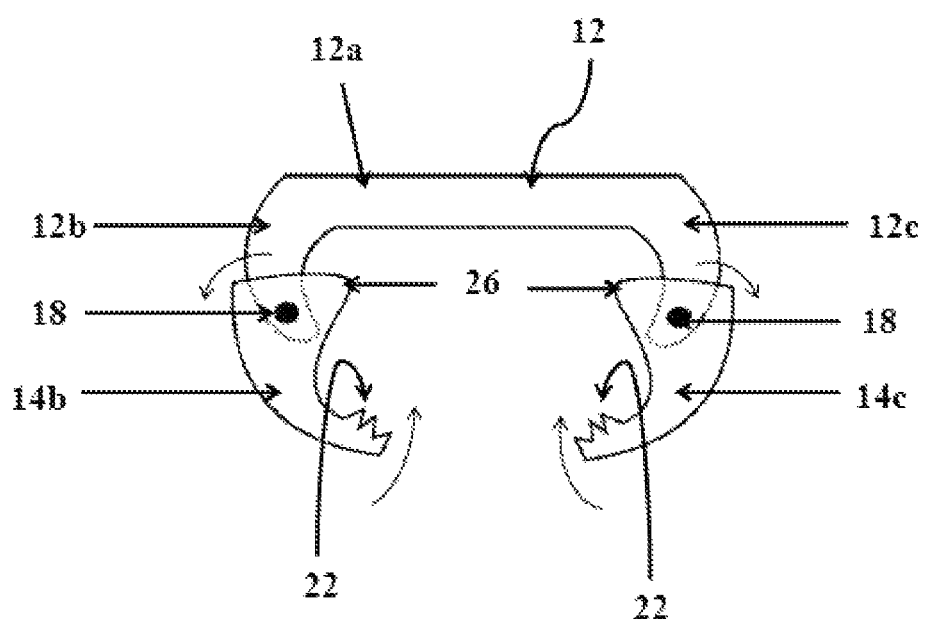
FIG. 1 illustrates a schematic drawing of the sternal closure device in its opened configuration.

According to this invention, there is provided a sternal closure and ribs approximator device, said device comprising:
- a substantially C-shaped shaft/bracket, said bracket comprising: a linear shaft and a pair of curvilinear arms at either ends of the shaft, respectively; and
- a pair of claw shaped clamping elements, each claw shaped clamping element coupling with an arm of the C-shaped shaft/bracket, near its end portion, said claw shaped clamping element being positioned such that the concavity of the claw faces the inner area determined by the arms of the C-shaped clamping shaft/bracket, the coupling being provided by means of a fastening mechanism such that angular displacement of the claw shaped clamping element about the pivoted fastening mechanism is provisioned, said claw shaped clamping elements adapted to be angularly displaced towards each other or away from each other, with the inner operative surface of each of the claw shaped clamping elements comprising a ridged surface for grasping.

In an embodiment of the invention, the substantially C-shaped shaft/bracket of the sternal closure and ribs approximator device shall include shaft/bracket of any shape that is known and obvious to person skilled in the art, wherein the shaft/bracket shall be capable to suitably perform same or similar function as that of the substantially C-shaped shaft/bracket.

In an embodiment of the invention, the sternal closure and ribs approximator device comprises at least one linear shaft.

In an embodiment of the invention, the C-shaped shaft comprises the linear shaft, wherein the said C-shaped shaft slide in and out or move over with the liner shaft with continuous contact with each other to obtain variable length.

In an embodiment of the invention, the end portion of the claw shaped clamping element comprises at least a pointed end.

In an embodiment of the invention, the device further comprises at least one chord attached to the pivot mechanism for further locking or tightening of the device.

In an embodiment of the invention, the tightening or relaxing movement of the device of the present invention is driven by at least one chord, wherein the tightening or relaxing of at least one chord enables locking or unlocking mechanism of the device.

The present invention in another embodiment provides a method of assembling a sternal closure and ribs approximator device, the method comprising the steps of:
- a) providing a single body C-shaped shaft/bracket comprising at least one linear shaft and at least a pair of curvilinear arms at the either ends of the shaft, wherein the C-shaped shaft/bracket and the linear shaft provides a broad base to the entire sternal closure and ribs approximator device; wherein the C-shaped shaft/bracket and the one linear shaft telescopes/slide in to the other in order to obtain variable length;
- b) coupling of at least one claw shaped clamping element with at least one curvilinear arm by a pivoted fastening mechanism, wherein a inner operative surface of the claw shaped clamping element comprises surface for grasping; and wherein the curvilinear arms in ends at least tipped or pointed manner.

The present invention in another embodiment provides a method for closing severed portions of a sternum using a sternal closure and ribs approximator device, the method comprises steps of:
- a) positioning and aligning a first and second opposed portions of a severed sternum for joining;
- b) placing the sternal closure and ribs approximator device about a respective opposed portions of the sternum, wherein a C-shaped shaft/bracket connecting and supporting the anterior portion of the sternum whereas a pair of claw shaped clamping element engaging the posterior surface of the sternum to maximize sternal healing;

c) adjusting the position of the sternal closure and ribs approximator device with respect to the portions of severed sternum d) fixing the severed sternum in an approximated position; and e) locking the sternal closure and ribs approximator device which enables the said device to secure the severed sternum firmly.

In an embodiment of the invention, one or more parts or components of the device of the present invention may be made up of any suitable biocompatible material such as but not limited to stainless steel, titanium, iron, cobalt, nickel, tantalum, zirconium, silver, gold, cobalt-chromium alloys, titanium alloys, nitinol, silicone rubber, acrylic resins, polyurethanes, polypropylene, polyethylene, polymethylmethacrylate, nylon, or ultra-high molecular weight polyethylene, polyglecaprone, polydioxanone and ceramics such as alumina, zirconia and hydroxyapatite, polylactides, polyglycolides, and copolymers thereof; poly(hydroxybutyric acid); poly(lactide-co-(ε-caprolactone-)); poly(glycolide-co-(ε-caprolactone)); polycarbonates, poly(pseudo amino acids); poly(amino acids); poly(hydroxyl alkanoate); polyanhydride or any combination thereof.

In an embodiment of the invention, one or more parts or components of the device of the present invention may be made up of any suitable metal such as but not limited to iron, copper, aluminum, gold, silver, bronze, platinum, tungsten, cadmium, zinc, tin, germanium, lead, nickel, tantalum, or any combination thereof.

In an embodiment of the invention, one or more parts or components of the device of the present invention may be coated with suitable therapeutic agent such as but not limited to antimicrobial agents, antibiotics, antiviral agents, anti-inflammatory agents, analgesic agents, haemostatic agents, anaesthetics, steroids, immunomodulating agents or agents such as bone morphogenic protein (BMP) or bone growth promoting agents or any combination thereof.

In an embodiment of the invention, the inner operative surface of the at least one claw shaped clamping element may comprise any shape of surface for grasping such as but not limited to projections, teeth, ridges, spikes, extensions, protrusions or any combination thereof.

In an embodiment of the invention, the device of the present invention may have high crack resistance, wear resistance, corrosion resistance and dimensional stability.

In embodiment of an invention, one or more parts or components of the device of the present invention may be coated with suitable coating material selected form the group of titanium and hydroxyapatite (HA), polytetrafluoroethylene (PTFE), ceramic, polymer or any combination thereof. The coating can be done to enhance biocompatibility, biostability, wear resistance, strength and lubricity.

In an embodiment of the invention, the device of the present invention is visible to different types of medical imaging such as but not limited to magnetic resonance imaging (MRI), tomography, x-ray, ultrasound, or any combination thereof.

In an embodiment of the invention, the device of the present invention is of any suitable cross sectional size or shape.

In an embodiment of the invention, the device and methods of the present invention may install, embed or connect one or more cameras to the system.

In an embodiment of the invention, the device of the present invention used in the surgical procedure such as but not limited to median sternotomy.

In an embodiment of the invention, the sternal closure and ribs approximator devices protects the sternum following the surgery and provide complete stability to sternum against the force acting on it such as but not limited to breathing, violent coughing, deep respiration, valsalva manoeuvre, physical shock, high blood pressure, muscle force, body fluid pressure or any combination thereof.

In an embodiment of the invention, at least the pair of the claw shaped clamping element and at least the pair of the curvilinear may be connected via spring such as but not limited to tension/extension spring, compression spring, torsion spring, constant spring, variable spring, coil spring, flat spring, machined spring, cantilever spring, coil spring or helical spring, compression springs, volute spring, tension or extension spring, hairspring or balance spring, leaf spring, v-spring, belleville washer or belleville spring, constant-force spring, gas spring, ideal spring, main spring, negator spring, progressive rate coil spring, rubber band, spring washer, torsion spring, wave spring or any combination thereof.

In an embodiment of the invention, the device and method of the present invention may be used to treat bone fractures such as but not limited to closed (simple) fracture, open (compound) fracture, complete fracture, incomplete fracture, linear fracture, transverse fracture, oblique fracture, spiral fracture, comminuted fracture, impacted fracture, avulsion fracture or any combination thereof.

In an embodiment of the invention, the device of the present invention may be adjustable to fit in groves and cavities along the surface of a sternal bone.

In an embodiment of the invention, at least one holder may be used to hold or secure the device of the present invention.

In an embodiment of the invention, one or more devices in accordance of the present invention may be coupled together and may be secured simultaneously by using at least one holder.

In an embodiment of the invention, the device of the present invention may consist of at least one breaking point. The breaking point allows easy and rapid dismantling of the components of the device.

In an embodiment of the invention, one or more devices in accordance of the present invention may be used for a single sternum, wherein the said sternal closure device may be used to secure first and second portions of severed sternum.

In an embodiment of the invention, the device and methods of the present invention may install, embed or connect one or more sensors to the system, such as but not limited to, temperature sensors, chemical sensors, pressure sensors, internal damage sensors, heart beat sensors, blood flow sensors, and the like, or a combination thereof. The sensors may be connected to a computing device or programmable logic controller, proportional-integral-derivative controllers. The combination of sensors and controllers may be used to monitor and control the device and methods of the present invention In an embodiment of the invention, the one or more parts or components of the system of the present invention may be connected and fixed, or may be detachable and re-attachable. detachable component can be attached or fixed with one or more of other components using mechanisms such as but not limited to screw threads, twist and lock mechanism, magnetic locking, vacuum induced locking, friction fit, snap fit, or any combination thereof.

In an embodiment of the invention, the components of the present invention may be connected or arranged by using any suitable method and may include without limitation use of one or more of welding, adhesives, riveting, fastening devices such as but not limited to screw, nut, bolt, hook, clamp, clip, buckle, nail, pin, ring.

DETAILED DESCRIPTION OF THE ACCOMPANYING DRAWINGS

In accordance with an exemplary embodiment of the invention, FIG. 1 represent a front view of the sternal closure device in its opened configuration, wherein there is provided a substantially C-shaped shaft/bracket (12), which is a single body. This comprises a linear shaft (12a) and a pair of curvilinear arms (12b, 12c) at either ends of the shaft, respectively. The C-shaped shaft/bracket (12) and the linear shaft (12a) provide a broad base to the entire sternal closure device. The claw shaped clamping elements (14b, 14c) couples by pivoted fastening mechanism (18) with an arms of the C-shaped shaft/bracket (12), near its end portion, wherein the inner corner edges (26) of the claw shaped clamping elements (14b,14c) supports or enables a pivot mechanism if an external pressure is exerted on the corner edges. The inner operative surface of each claw shaped clamping elements (14b, 14c) comprises a ridged surface (22) for grasping.

Figure 2:
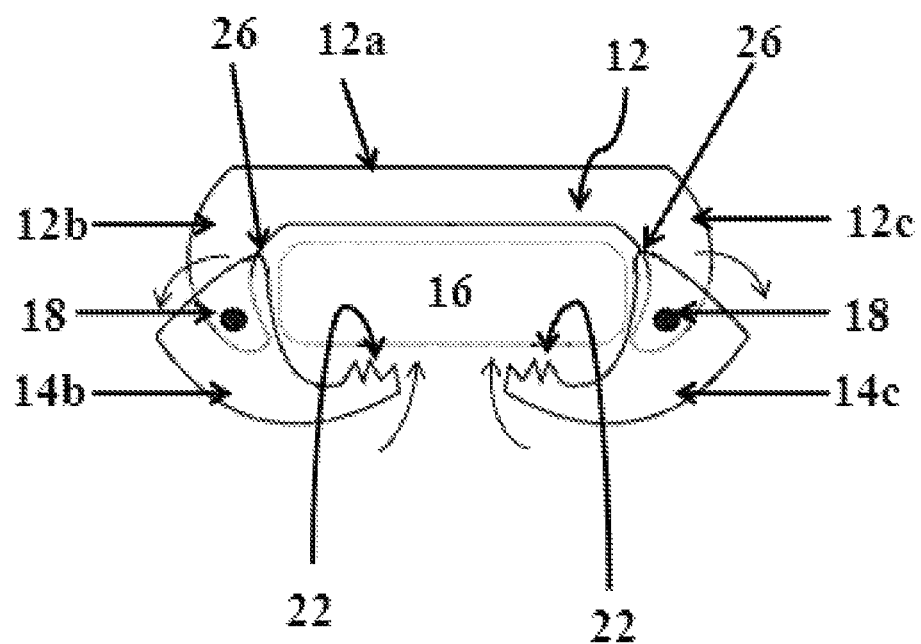
FIG. 2 illustrates a schematic drawing of the sternal closure device in its closed configuration.
Figure 3:
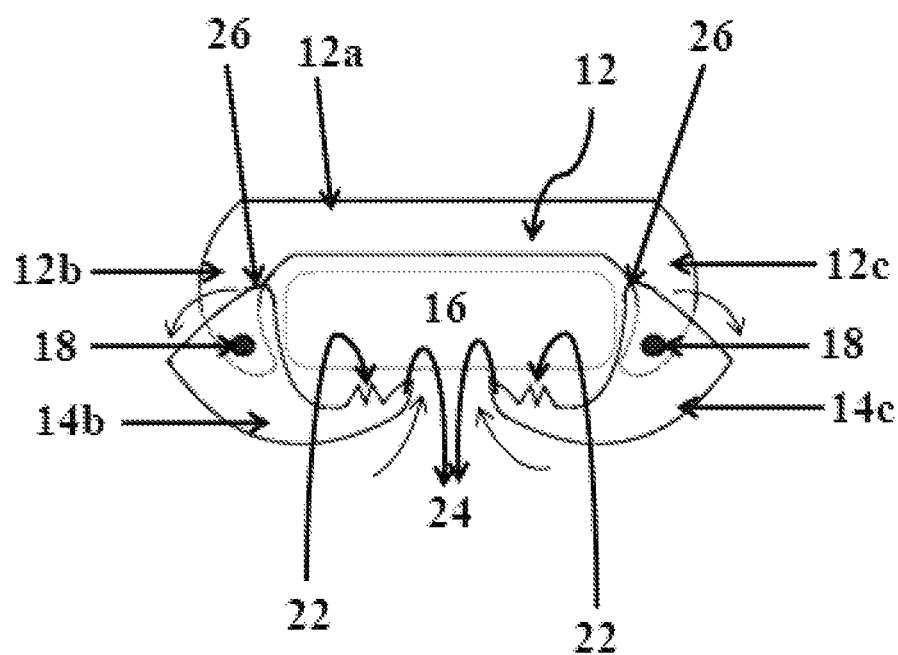
FIG. 3 illustrates an alternative schematic drawing of the sternal closure device in its closed configuration.

In accordance with an exemplary embodiment of the invention, FIG. 2 and FIG. 3 represent a front view of the sternal closure device in its closed configuration, wherein the claw shaped clamping element (14b, 14c) is positioned such that the concavity of the claw faces the inner area (16). The clawed curvilinear arms end in tipped or pointed manner (24). Further the inner operative surface of each claw shaped clamping elements (14b, 14c) comprises a ridged surface (22) for grasping.

Figure 4:
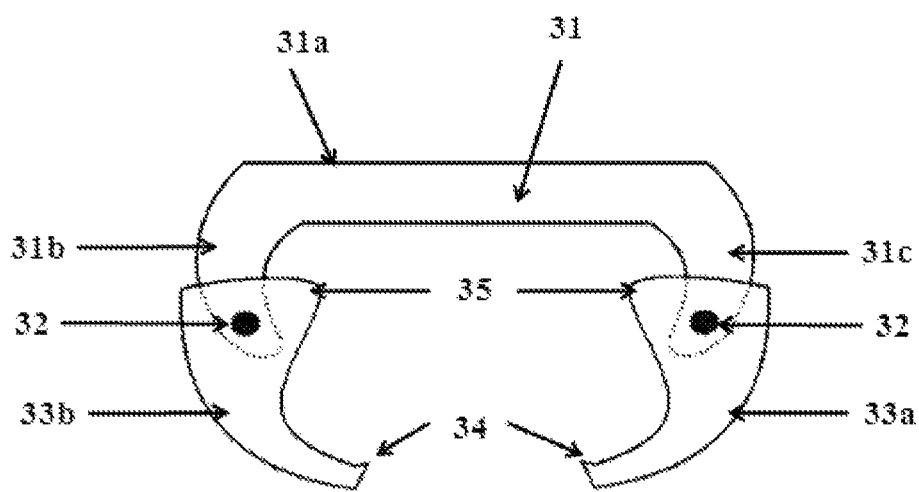
FIG. 4 illustrates a schematic drawing of one embodiment of the sternal closure device in its opened configuration.

In accordance with an exemplary embodiment of the invention, FIG. 4 represents a front view of the sternal closure device in its opened configuration, wherein there is provided a substantially C-shaped shaft/bracket (31), which is a single body. This comprises a linear shaft (31a) and a pair of curvilinear arms (31b, 31c) at either ends of the shaft, respectively. The C-shaped shaft/bracket (31) and the linear shaft (31a) provide a broad base to the entire sternal closure device. The claw shaped clamping elements (33a, 33b) end in tipped or pointed manner (34) and couples by pivoted fastening mechanism (32) with an arms of the C-shaped shaft/bracket (31), near its end portion, wherein the inner corner edges (35) of the claw shaped clamping elements (33a, 33b) supports pivot mechanism.

Figure 5:
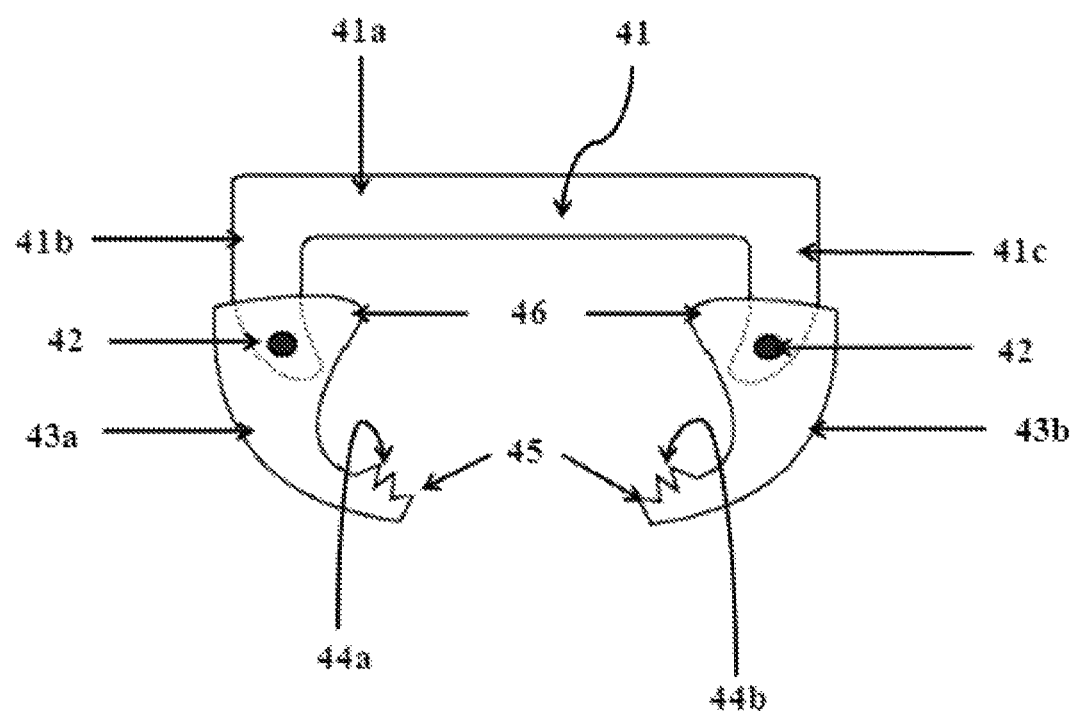
FIG. 5 illustrates a schematic drawing of the sternal closure device in its opened configuration, wherein an arrangement of substantially square shaped shaft and claw shaped clamping elements is shown.

In accordance with an exemplary embodiment of the invention, FIG. 5 represents a front view of the sternal closure device wherein there is provided a substantially square-shaped shaft (41), which is a single body. This comprises a linear shaft (41a) and a pair of square shaped arms (41b, 41c) at either ends of the shaft, respectively. The C-shaped shaft/bracket (41) and the linear shaft (41a) provide a broad base to the entire sternal closure device. The claw shaped clamping elements (43a, 43b) couples by pivoted fastening mechanism (42) with an arms of the square-shaped shaft (41) near its end portion, wherein the inner corner edges (46) of the claw shaped clamping elements (43a, 43b) supports pivot mechanism. The claw shaped clamping elements (43a, 43b) end in tipped or pointed manner (45), wherein the inner operative surface of each claw shaped clamping elements (43a, 43b) comprises a ridged surface (44a, 44b) for grasping.

Figure 6:
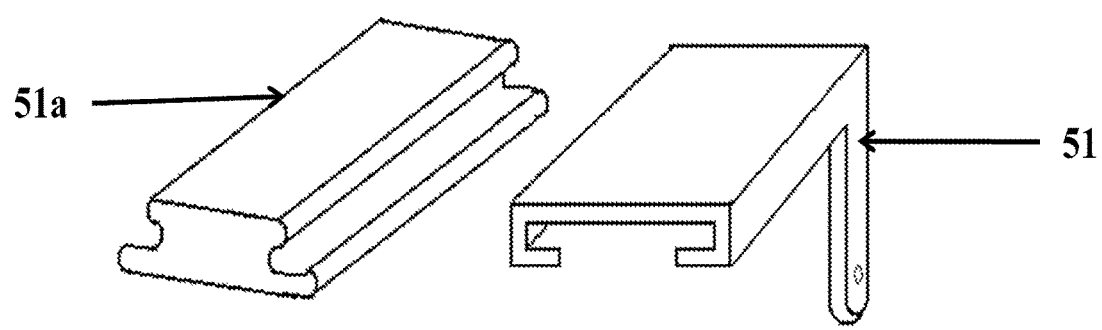
FIG. 6 illustrates an example of an isometric view of a C-shaped shaft and linear shaft.

In accordance with an exemplary embodiment of the invention, FIG. 6 represents an isometric view of a C-shaped shaft (51) and a linear shaft (51a), wherein the C-shaped shaft (51) slides in and out or moves along the liner shaft (51a) with continuous contact with each other to obtain variable length.

Figure 7:
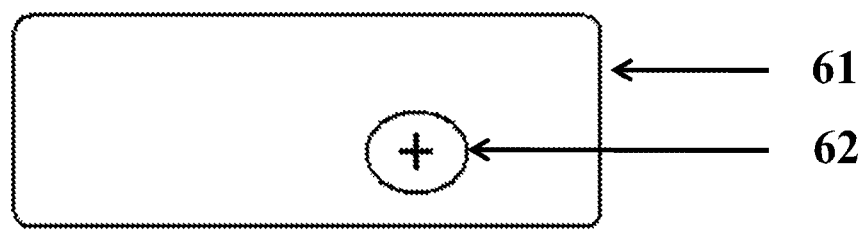
FIG. 7 illustrates an example of a top view of a locking arrangement is shown.

In accordance with an exemplary embodiment of the invention, FIG. 7 represents a top view of a locking arrangement (61), wherein the locking arrangement is mounted on the top surface of the C-shaped shaft. The locking arrangement enables the locking or unlocking of a sternal closure device.

Figure 8:
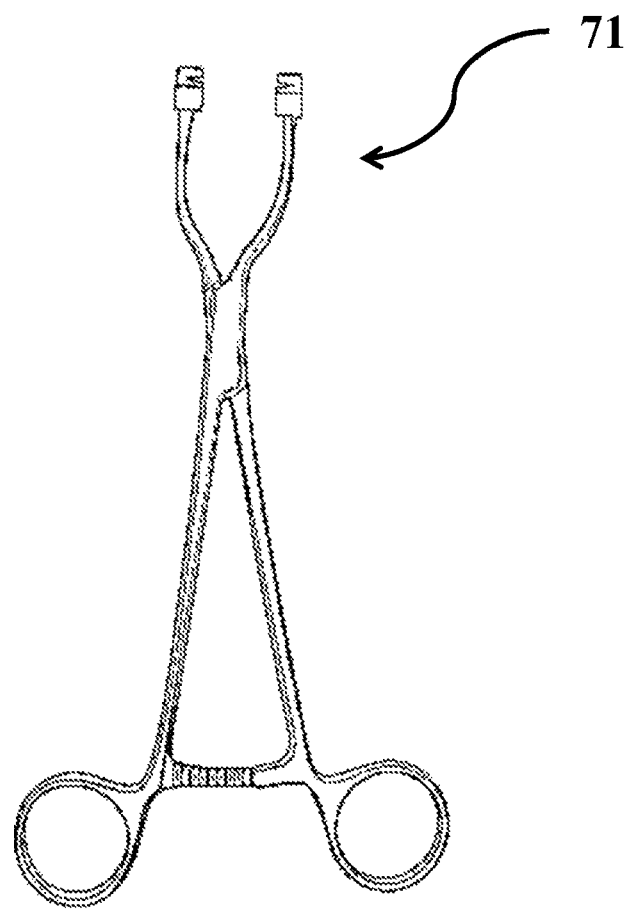
FIG. 8 illustrates an example of a front view of a holder.

In accordance with an exemplary embodiment of the invention, FIG. 8 represents a front view of a holder (71), wherein the holder (71) is used to place or secure a sternal closure device.

Figure 9:
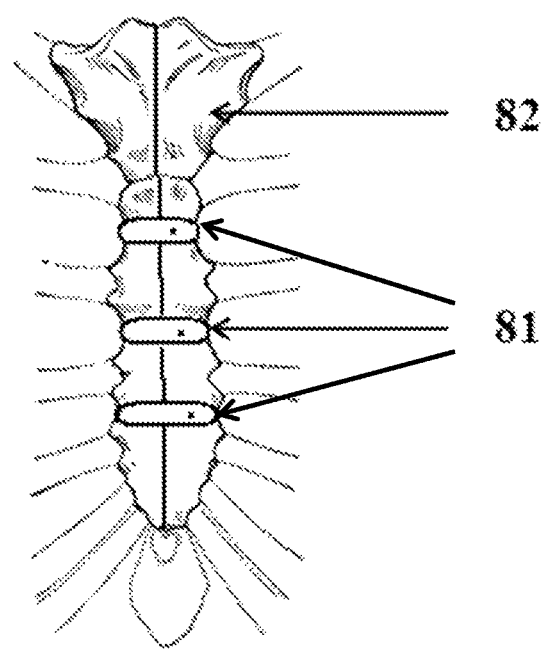
FIG. 9 illustrates an exemplary view of multiple sternal closure devices applied to a single sternum.

In accordance with an exemplary embodiment of the invention, FIG. 9 represents at view showing multiple sternal closure devices being used for a single sternum, wherein the said sternal closure devices (81) used to secure first and second portions of severed sternum (82).

The term "sternal closure device" and "sternal closure and ribs approximator_device" may be alternatively used for the purpose of the present invention.

The terminology used herein is for the purpose of describing particular embodiments only and is not intended to be limiting of the invention. As used herein, the singular forms "a", "an", and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude or rule out the presence or addition of one or more other features, integers, steps, operations, elements, components, and/or groups thereof.

While this detailed description has disclosed certain specific embodiments of the present invention for illustrative purposes, various modifications will be apparent to those skilled in the art which do not constitute departures from the spirit and scope of the invention as defined in the following claims, and it is to be distinctly understood that the foregoing descriptive matter is to be interpreted merely as illustrative of the invention and not as a limitation.

I claim:

1. A sternal closure and ribs approximator device for joining of a severed and fractured portions of a sternum, comprising:
   a) a C-shaped shaft/bracket (12) comprising a linear shaft (12a) and at least a pair of curvilinear arms (12b and 12c);
   b) at least a pair of claw shaped clamping elements (14b and 14c); and
   c) a pair of fastening mechanism (18) pivotally holding the at least a pair of claw shaped clamping elements (14b and 14c) to the curvilinear arms (12b and 12c) of the C-shaped shaft/bracket (12) directly attached to free ends of the curvilinear arms (12b and 12c)/for pivotal movement in same plane as of the curvilinear arms (12b and 12c);
   wherein the C-shaped shaft/bracket (12) comprising the linear shaft (12a) and the at least a pair of curvilinear arms (12b and 12c) is a single body, and wherein the C-shaped shaft/bracket (12) provides a broad base for attachment to the severed and fractured portions of sternum; and
   wherein the pair of claw shaped clamping elements (14b and 14c) incorporate a concavity facing an inner area (16) that lies between the pair of curvilinear arms (12b and 12c) of the C-shaped clamping shaft/bracket (12) for grasping the severed sternum portions.

2. The sternal closure and ribs approximator device of claim 1, wherein the C-shaped shaft/bracket (51) slides in and out or moves over with the liner shaft (51a) with continuous contact with each other to obtain variable length.

3. The sternal closure and ribs approximator device of claim 1, wherein the pair of fastening mechanism (18) enables angularly displacement of the at least a pair of the claw shaped clamping elements (14b and 14c) towards each other or away from each other.

4. The sternal closure and ribs approximator device of claim 1, wherein the end portion of each of the claw shaped clamping elements (14b and 14c) comprises at least a pointed shape (24).

5. The sternal closure and ribs approximator device of claim 1, wherein an inner operative surface of each claw shaped clamping element (14b and 14c) has at least a ridged surface (22) for grasping.

6. The sternal closure and ribs approximator device of claim 1, wherein the device further incorporates a locking arrangement (61) mounted on top surface of the C-shaped shaft/bracket (12) to enable a locking or an unlocking of the device.

7. The sternal closure and ribs approximator device of claim 1, wherein one or more parts or components of the device are made up of a suitable biocompatible material selected from a group consisting of stainless steel, titanium, iron, cobalt, nickel, tantalum, zirconium, silver, gold, cobalt-chromium alloys, titanium alloys, nitinol, silicone rubber, acrylic resins, polyurethanes, polypropylene, polyethylene, polymethylmethacrylate, nylon, ultra-high molecular weight polyethylene, polyglecaprone, polydioxanone, ceramics, polylactides, polyglycolides, poly(hydroxybutyric acid), poly(lactide-co-(s-caprolactone-)), poly(glycolide-co-(s-caprolactone)), polycarbonates, poly(pseudo amino acids), poly(amino acids), poly(hydroxyl alkanoate), polyanhydride, copolymers, and a combination thereof.

8. The sternal closure and ribs approximator device of claim 1, wherein parts or components of the device are coated.

9. The sternal closure and ribs approximator device of claim 1, wherein a pivot movement of the claw shaped clamping element is configured to be guided by relative interaction between inner corner edges of the claw shaped clamping element with sternal bone of a patient.

* * * * *